(12) United States Patent
Zhadanov et al.

(10) Patent No.: US 6,228,066 B1
(45) Date of Patent: May 8, 2001

(54) INJURY RESISTANT NEEDLE DEVICE

(76) Inventors: Sam Zhadanov; Eli Zhadanov, both of 2944 W. 5th St. Apt. 20J, Brooklyn, NY (US) 11224

( * ) Notice: Subject to any disclaimer, the term of this patent is extended or adjusted under 35 U.S.C. 154(b) by 0 days.

(21) Appl. No.: 09/337,002

(22) Filed: Jun. 28, 1999

(51) Int. Cl.$^7$ ..................................................... A61M 5/32
(52) U.S. Cl. ............................................. 604/198; 604/110
(58) Field of Search .................................. 604/192, 198, 604/164.08, 165.02, 165.04, 166.01, 272, 110, 197

(56) References Cited

U.S. PATENT DOCUMENTS

| | | | |
|---|---|---|---|
| 5,067,946 | * 11/1991 | Zhadanov | ........................ 604/272 X |
| 5,154,699 | * 10/1992 | Ryan | ................................ 604/192 X |
| 5,997,485 | * 12/1999 | Ahmadzadeh | .............. 604/164.12 X |

* cited by examiner

*Primary Examiner*—Anhtuan T. Nguyen
(74) *Attorney, Agent, or Firm*—I. Zborovsky

(57) ABSTRACT

An injury resistance needle device has an outer protective tube, a needle unit having a needle which is movable relative to the outer protective tube between an extended position in which the needle is exposed outside of the outer protective tube and a retracted position in which the needle is completely confined inside the outer protective tube, a plurality of first engaging formations provided on the needle unit, and a rotary member provided with the second interengaging formations interengageable with the first engaging formations and turnable by a user, and a unit for turning the rotary member by a user, the turning unit being formed so that when a user acts initially on the turning means the rotary member is turned for displacing the needle unit from the extended position to the retracted position and during a further action by the user the turning unit is deactivated so as not to allow turning of the rotary member.

2 Claims, 2 Drawing Sheets

INJURY RESISTANT NEEDLE DEVICE

BACKGROUND OF THE INVENTION

The present invention relates to injury resistant needle devices for blood collection, intravenous use, etc.

Needles for blood collection and for intravenous use are widely utilized. After respective operations of blood collection or intravenous use, there is a possibility of injuring of personnel of the exposed end of the needle. In order to prevent such an injury, many devices have been designed to cover the needle end after the use. One of such devices was invented by us as disclosed in U.S. Pat. No. 5,067,946. In this device the needle unit which has a needle has first engaging formations, and the rotary member is turnable by a user, has second engaging formations which engage with the first engaging formations so that by turning the rotary member the needle unit is displaced between an exposed position in which a needle is located outside of a protective tube and a retracted position in which the needle is completely confined inside the protective tube. This construction can be further improved.

SUMMARY OF THE INVENTION

Accordingly, it is an object of present invention to provide an injury resistant device which is a further improvement of the existing devices.

In keeping with these objects and with others which will become apparent hereinafter, one feature of present invention resides, briefly stated, in a injury resistant needle device which has an outer protective tube, a needle unit having a needle which is movable relative to the outer protective tube between an extended position in which the needle is exposed outside of the outer protective tube and a retracted position in which the needle is completely confined inside the outer protective tube, means for moving the needle unit between the extended and retracted positions, the moving means including a plurality of first engaging formations provided on the needle unit, and a rotary member provided with the second interengaging formations interengageable with the first engaging formations and turnable by a user, and means for turning the rotary member by a user, the turning means being formed so that when a user acts initially on the turning means the rotary member is turned for displacing the needle unit from the extended position to the retracted position and during a further action by the user the turning means is deactivated so as not to allow turning of the rotary member.

When the injury resistant needle device is designed in accordance with present invention, it provides for an additional protective in reliably confining the needle after the use inside the protective tube.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
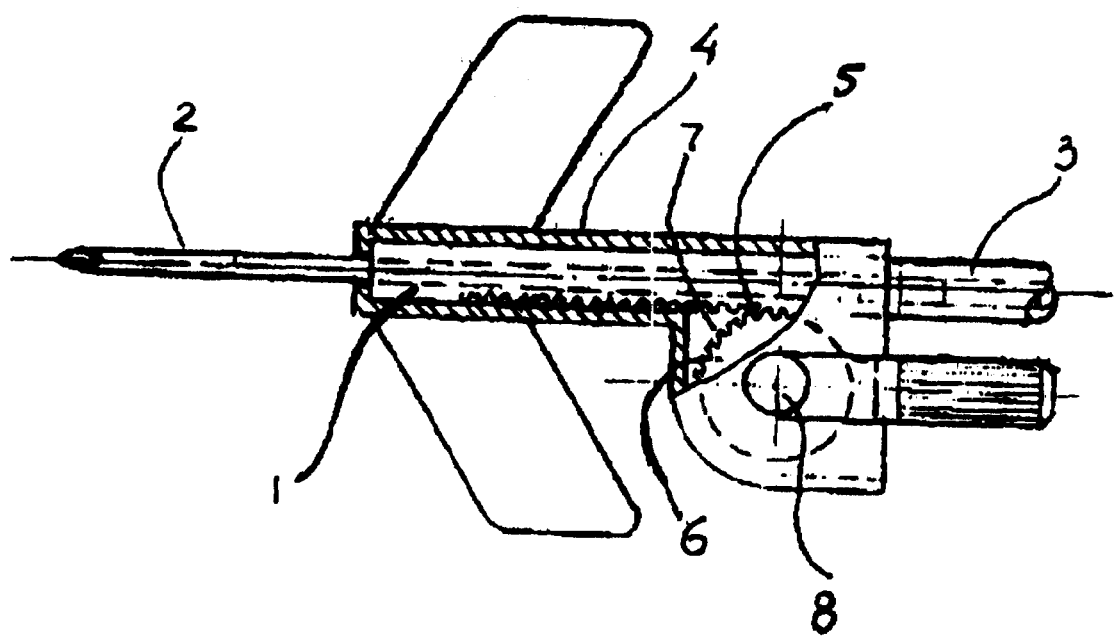
FIG. 1 is a side view of an injury resistant needle device in accordance with present invention.

An injury resistant device in accordance with present invention has a needle unit which is identified as a whole with reference numeral 1. The needle unit 1 includes a needle 2 which is held with an inner tubular member 3. The needle device in accordance with the present invention is further with an outer protective tube identified with reference numeral 4. The outer protective tube 4 has an inner opening through which the tubular member 3 with the needle 2 can move between an extended position shown in the drawings and a retracted position which is not shown in the drawings. In the extended position the needle is exposed outwardly beyond the protective tube 4, while in the retracted position the needle 2 is completely retracted into the protective tube 4.

The inventive injury resistant needle device has further means for moving the needle unit 1 between the extended position and the retracted position. The moving means include a plurality of engaging formations identified with reference numeral 5 and provided on the inner tubular member 3. The engaging formations 5 can be formed as a plurality of teeth. The moving means further include a rotary member 6 which can be formed as a small wheel with a plurality of teeth 7 engageable with the teeth 5 of the inner tubular member.

The shaft 8 of the wheel 6 extends through a transverse opening 9 in two upstanding flanges of the outer protective tube 4 The shaft 8 is connected with the rotary member 6 for example by knurling provided on the adjoining surfaces of the shaft 8 and the rotary member 6 and identified with reference numeral 9.

The injury resistant needle device in accordance with present invention further has means for turning the rotary member 6. The turning means include a flexible shaft connected with the 8.

The flexible shaft has a further part 10 which is formed as a handle provided with outer knurling, and a flange 11 directly connected with the shaft 8. The handle 10 is connected with the flange 11 by a thin material transition 14 formed for example as a very short strip, etc. The handle 10 is connected with an engaging catch 12 provided with a tooth.

Figure 2:
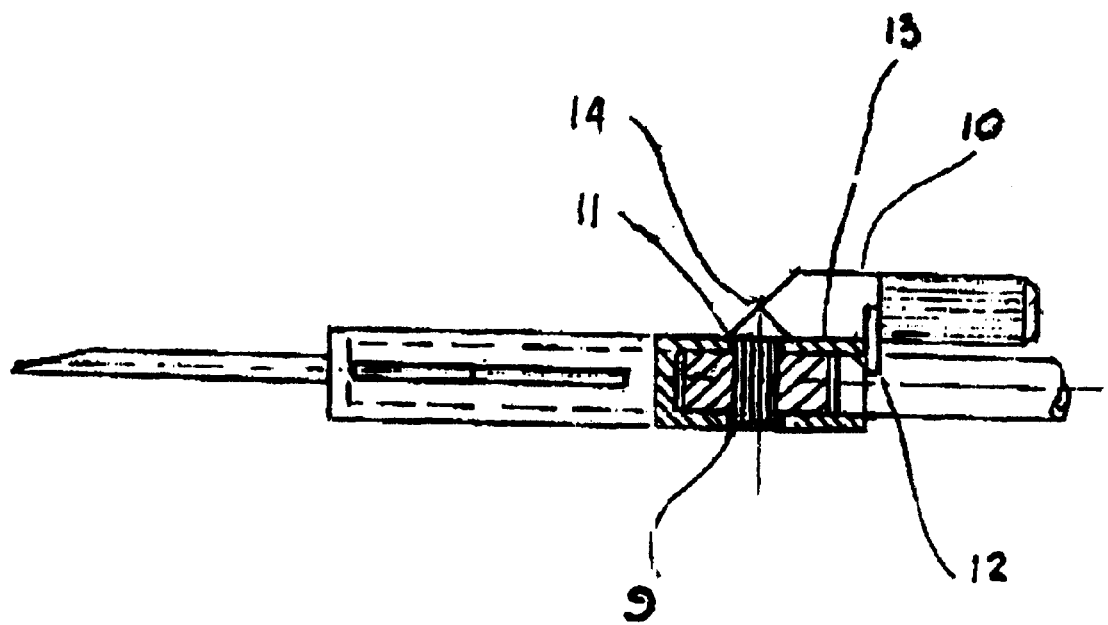
FIG. 2 is a plan view of the injury resistant device of FIG. 1.
Figure 3:
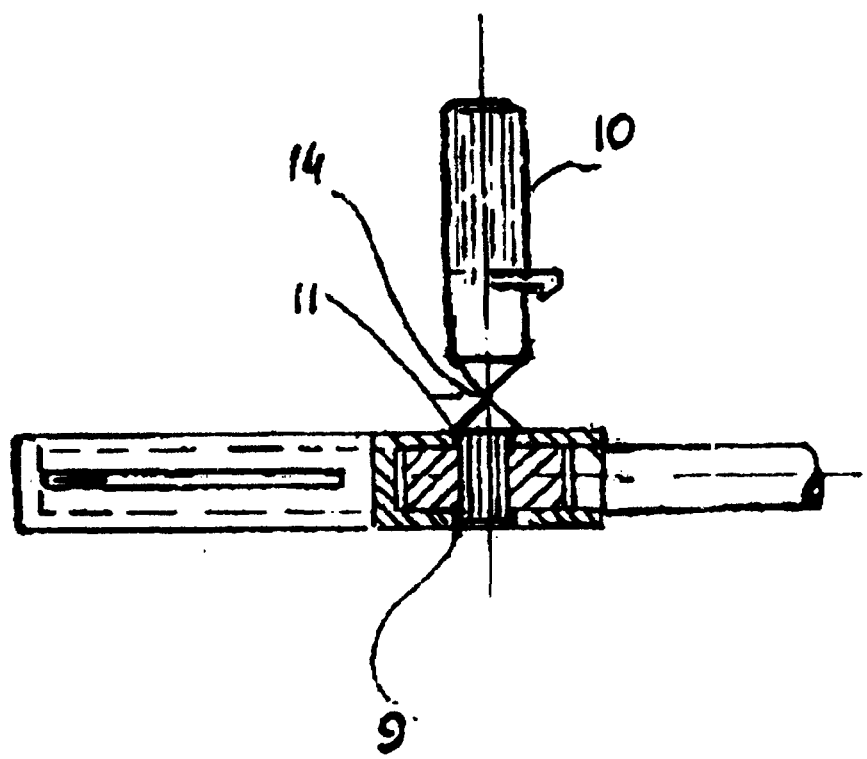
FIG. 3 is a plan view of the injury resistant needle device with the needle in an inoperative position.
Figure 4:
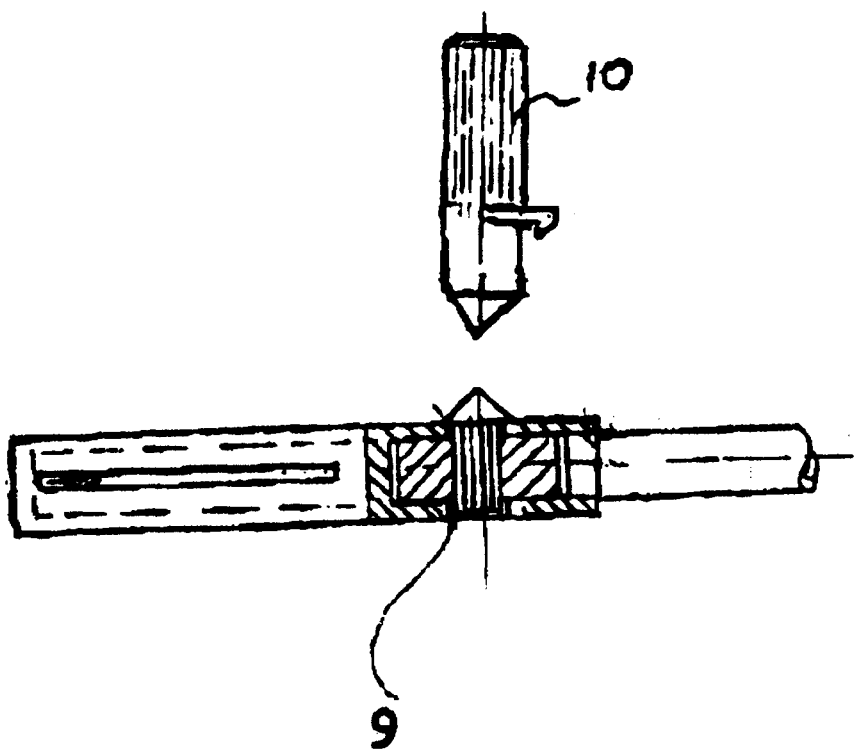
FIG. 4 is a view substantially corresponding to the view of FIG. 3, but showing needle unit turning means in a position in which the needle unit no longer can be exposed.

In the operative position shown in FIG. 2 of the drawings in solid lines, the handle is located so that it is coextensive with the needle unit, its catch 12 engages behind the end portion of the protective tube 4, and its surface abuts against an outer surface 13 of the protective tube 4. In this position, the needle device can be used for collecting blood, intravenous use, etc. After the corresponding time of operation, it is necessary to retract the needle 2 so as to confine it completely inside the protective tube 4. For this purpose a user turns the handle 10 from the position shown in FIG. 2 to the position shown in FIG. 2, with a disengagement of the catch 12 from the protective tube 4. The user turns the handle 10 around its axis and through the connecting transition 14 also turns the shaft 8 and the rotary member 9 so that the rotary member 9 displaces the needle unit to the right at the drawings until the needle 2 including its left end is completely confined inside the space of the protective tube 4. During further turning of the handle 10 by the user the connecting transition 14 is twisted and finally broken so as to disconnect the handle 10 from the flange 11, as shown in FIG. 4. After this, it is no longer possible to turn the shaft 8 and the rotary member 5 and therefore there is no risk of moving the needle 2 into a position in which it is exposed outside of the protective tube 4.

It will be understood that each of the elements described above, or two or more together, may also find a useful application in other types of constructions differing from the types described above.

While the invention has been illustrated and described as embodied in injury resistant needle device, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An injury resistant needle device, comprising an outer protective tube; a needle unit having a needle which is movable relative to said outer protective tube between an extended position in which said needle is exposed outside of said outer protective tube and a retracted position in which said needle is completely confined inside said outer protective tube; moving means for moving said needle unit between said extended and retracted positions said moving means including a plurality of first engaging formations provided on said needle unit, and a rotary member provided with second engaging formations interengagable with said first engaging formations and turnable by a user; and turning means for turning said rotary member by a user, said turning means being formed so that when a user acts initially on said turning means said rotary member is turned for displacing said needle unit from said extended position to said retracted position and during a further action by the user said turning means is deactivated so as not to allow turning of said rotary member, said turning means being connected with said rotary member so that during said initial action by the user said turning means turns said rotary member, and during said further action by the user said turning means is broken so that a users turning action no longer can be transmitted to said rotary member.

2. An injury resistant needle device, comprising an outer protective tube; a needle unit having a needle which is movable relative to said outer protective tube between an extended position in which said needle is exposed outside of said outer protective tube and a retracted position in which said needle is completely confined inside said outer protective tube; moving means for moving said needle unit between said extended and retracted positions said moving means including a plurality of first engaging formations provided on said needle unit, and a rotary member provided with second engaging formations interengagable with said first engaging formations and turnable by a user; and turning means for turning said rotary member by a user, said turning means being formed so that when a user acts initially on said turning means said rotary member is turned for displacing said needle unit from said extended position to said retracted position and during a further action by the user said turning means is deactivated so as not to allow turning of said rotary member, said turning means being connected with said rotary member so that during said initial action by the user said turning means turns said rotary member, and during said further action by the user said turning means is broken so that a users turning action no longer can be transmitted to said rotary member, said turning means including a thin connecting strip which is formed so as to transmit rotation applied by a user from said turning means to said rotary member and during said further action by the user said strip is broken and does not transmit the rotation.

\* \* \* \* \*